United States Patent
Song et al.

(10) Patent No.: US 6,342,252 B1
(45) Date of Patent: Jan. 29, 2002

(54) PROCESS FOR PRODUCING A BIO-ORGANIC CALCIUM COMPOSITION AND NUTRIENT AGENT CONTAINING THE SAME

(75) Inventors: Juntong Song; Xigui Yuan, both of Tianjin (CN)

(73) Assignee: Tianjin Tianshi Group Co., Ltd., Tianjin (CN)

( * ) Notice: Subject to any disclaimer, the term of this patent is extended or adjusted under 35 U.S.C. 154(b) by 0 days.

(21) Appl. No.: 09/423,584

(22) PCT Filed: Mar. 10, 1998

(86) PCT No.: PCT/IB98/00308

§ 371 Date: Mar. 9, 2000

§ 102(e) Date: Mar. 9, 2000

(87) PCT Pub. No.: WO99/45798

PCT Pub. Date: Sep. 16, 1999

(51) Int. Cl.[7] .................. A61K 35/32; A61K 35/34; A61K 35/12

(52) U.S. Cl. .................. 424/549; 424/548; 424/520

(58) Field of Search .................. 424/549, 548, 424/520

(56) References Cited

FOREIGN PATENT DOCUMENTS

| JP | 59-192066 | * 10/1984 |
| JP | 07-75527 | * 3/1995 |

* cited by examiner

Primary Examiner—Christopher R. Tate
Assistant Examiner—Brett Ozga
(74) Attorney, Agent, or Firm—Heller Ehrman White & McAuliffe LLP

(57) ABSTRACT

A process of producting bio-organic calcium composition from animal bones comprises steps of preliminarily removing lipids from the bones by steaming/boiling; milling the bones to form a bone slurry; adding neutral lipase to conduct secondary lipid removing; adding protease to the bone slurry to produce a primary enzymatic decomposed liquid; adding papain to the primary enzymatic decomposed liquid for producing secondary enzymatic decomposed liquid; and acidifying/activating of the secondary enzymatic decomposed liquid to produce a final product. The product produced by this process contains bio-organic calcium composition readily absorbable by human body.

20 Claims, No Drawings

PROCESS FOR PRODUCING A BIO-ORGANIC CALCIUM COMPOSITION AND NUTRIENT AGENT CONTAINING THE SAME

TECHNICAL FIELD

The present invention relates to a process for producing a bio-organic calcium composition mainly based on amino acid-calcium chelates and/or peptide-calcium chelates, and an oral nutrient agent comprising the thus produced amino acid-calcium chelates and/or peptide-calcium chelates composition.

BACKGROUND ART

It has been known for long that calcium is one of the fundamental elements of human body. Calcium plays an active role in many physiological activities of human body, such as modulating muscle function, blood flow of capillary, participating in blood coagulation and nerve impulse transfer, and maintaining heart beat rate, etc. If human body is in short of calcium, many kinds of diseases may occur. For example, if a woman in pregnancy or in wet nurse lacks of calcium, it is harmful to the growth of fetus, causing unhealthy teeth and bones, poor blood coagulation, and muscle convulsion, etc. With long term lacking of calcium, children may grow with unhealthy bones, even become rickets, and elder human may have loose bones and bone hyperplasia. Lacking of calcium may also be a factor of inducing hypertension, diabetics, vascular sclerosis, and elder dementia. It is very important to provide adequate calcium supply to human since calcium can not be produced by human body and can only be absorbed from food. However, since customs, habits, feed behaviors and food structures are so widely not alike in countries and nationals, the actual daily absorption of calcium are quite different. It has been reported that lacking of calcium is a world wide problem. In many countries, calcium provided by dietary is not enough comparing to the calcium needed by a human body. In some countries, standards for daily minimum calcium supply to a human have been set up. For example, such a standard is 1,000 mg/day for an adult human, and 1,500 mg/day for junior in the United States of America. Similarly, a standard of daily calcium supply in China is 800 mg/day. However, the actual daily calcium supply in China is less than 500 mg/day due to the lacking of diary products in food structure. It has been reported that there is about 900 million people without enough calcium supply in China.

At the present, various kinds of calcium supplement products are available to human. However, these products have a poor actual absorbing rate to human. It has been known for long time that the calcium absorption is mainly occurred in human intestine. Only soluble calcium ions in intestine can be absorbed. But, since the pH in intestine is normally in the range of about 7.2–7.8, this weak basic condition makes the most calcium contained in these supplement product insoluble and can not be absorbed at all in human intestine. This phenomena often occurs with inorganic calcium, such as calcium chloride, calcium hydroxide, calcium oxide, etc. On the hand, organic calcium products, such as calcium gluconate, calcium lactate, and calcium citrate, etc. are more soluble comparing with inorganic calcium. But, the problem with these organic calcium products is that their calcium content is very low in general. Even taking large amount of these organic calcium products, the actual absorption of calcium still can not reach the needed level.

Recent studies in the theory and mechanism of the chelate of amino acid and calcium disclose that mineral elements can be chelated with amino acid to form an "amino acid-mineral element chelate". This amino acid-mineral element chelate is soluble in the basic fluid of pH above 7.0, such as in intestine fluid, and can be absorbed by the epithelial cell of intestine during the active transportation of amino acid. Thus, mineral elements, such as calcium contained in these chelates, is transported into blood. In this process, amino acid plays a role of carrying mineral ions while itself is useful to human body. After the amino acid-calcium chelate is transported into blood, it forms a sustained releasing "mobile calcium pool" in the blood. This "mobile calcium pool" continues to release $Ca^{2+}$ to meet the needs of bones, nerve system, and muscles. This mobile calcium pool neither causes $Ca^{2+}$ concentration in blood harmfully high nor increases the $Ca^{2-}$ excretion by kidney. Therefore, this amino acid-calcium chelate has been considered as the most efficient way of supplement of calcium. In accordance with the theory of amino acid-calcium chelate, peptide with molecular weight less than 1,500 Dalton can also form peptide-mineral ion chelate with mineral elements. Then, this chelate of amino acid-mineral ion can be absorbed by human body through the active amino acid transportation of the epithelial cells of intestine. This theory of amino acid-calcium chelate also indicates that under the appropriate condition, calcium and proteins can become ions and peptide and/or amino acid suitable for chelating, respectively, whereby to form readily absorbable peptide-calcium chelates and amino acid-calcium chelates.

It has been known for long that animal bones contain calcium and protein. Many attempts have been conducted to utilize fresh animal bones to produce edible proteins. U.S. Pat. No. 5,163,129 disclosed a particulate proteinaceous product and methods for producing the same from waste raw animal parts, which comprises crushing the raw materials to produce a suspension, hydrolyzing proteins with protease, heating to inactivate enzymes, screening, concentrating, pasteurizing, removing water, and separating oil. The final products contain non-denatured protein, oil, amino acids, and metal ions.

U.S. Pat. No. 4,420,723 disclosed a method for converting blood, animal parts, bone wastes into partial hydrolyzed protein, which comprises comminution of the starting material, adding water, acid or base to adjust pH, heating, cooling, adding proteinase, such as papain and pancreatic amylase to conduct enzymatic decomposition, filtration (including deactivate enzyme). concentrating and pasteurizing, removing lipid by centrifuge, and spray drying to obtain homogenized final products.

U.S. Pat. No. 4,176,199 disclosed a method of extracting proteins from beef bones by crushing the bones to a determined size, cooking the bones, adding papain to conduct enzymatic decomposition, filtration, and removing lipid by centrifuge.

U.S. Pat. No. 4,473,589 disclosed a method of producing liquid protein product from residues and waste products, such as fish, poultry, pork and beef, which comprises alkaline treatment with heat and alkali, and adding protease for enzymatic decomposition. The final products may be conserved with various acids.

U.S. Pat. No. 4,452,888 disclosed a method of producing low molecular weight peptide composition, which comprises adding water and acid to adjust pH, and adding at least two acid proteases to conduct enzymatic decomposition. Final product contains low molecular peptides.

U.S. Pat. No. 4,402,873 disclosed a method of producing proteins from fresh or cured pork bones, which comprises comminution, adding water, heating, adding papain to conduct enzymatic decomposition, deactivate enzyme by heating, rapid cooling, separate liquid from solids, centrifuging the liquid phase to produce liquid protein, then concentrating to final product.

None of any prior simple means or procedures economically produce high content bio-organic calcium from animal bones. Prior arts focused on extracting of proteins. The products of the prior arts contains very little calcium. Therefore, what is needed is a high efficient calcium product that can provide sufficient absorbable bio-organic calcium to human and the production process thereof.

An objective of the present invention is to produce a bio-organic calcium composition mainly containing peptide-calcium chelates and/or amino acid-calcium chelates.

Another objective of the present invention is to produce a bio-organic calcium composition containing very low lipids.

A further objective of the present invention is to produce a bio-organic calcium composition containing additional nutritious component, such as amino acids and peptides.

A further objective of the present invention is to produce a nutrient agent containing the bio-organic calcium composition.

It is a still further objective of the present invention to provide a process for producing a bio-organic calcium composition mainly based on peptide-calcium chelates and/or amino acid-calcium chelates.

DISCLOSURE OF INVENTION

The process in accordance with the present invention produces a bio-organic calcium product from fresh animal bones. In accordance with a preferred embodiment of the present invention, the process comprises basic stages of washing and cleaning fresh beef bones, frozen, comminuting bones to form a suspension, removing lipid/oil with steaming/boiling under appropriate pressure and temperature, conducting enzymatic decomposition for further removing lipid/oil, carrying out biochemical treatment to reduce the collagen and phosphoprotein to low molecular weight peptides and amino acids, acidic activation, neutralization, deodorization, and spray drying.

It is the most important feature of the present invention that the calcium hydrophosphate contained in animal bones releases $Ca^{2+}$ by acidic activation. The released $Ca^{2+}$ is chelated with peptides and/or amino acids to form bio-organic calcium readily absorbable to human body.

After the acidic activation, calcium hydroxide is used for neutralizing the acids. This treatment not only avoids the sodium ions being presented in the final product, but also increases the calcium content in the final products.

It is preferred to utilize fresh beef bones as raw materials because over 90% calcium of an animal is located in bones. Collagen and phosphoprotein are rich in animal bones. Trace mineral elements and vitamins contained in animal bones are far more rich than that of meat. However, nutrition contents are different among bones, for example, bones that are more active in basic metabolism, such as vertebrate bones and ribs contain much more nutrition than other bones. Vertebrate bones and ribs also contain more $Ca^{2+}$ than others. The preferred raw materials for the process in accordance with the present invention are fresh beef vertebrate bones and ribs.

In accordance with one preferred embodiment of the present invention, lipids/oil are repeatedly removed because they are harmful to human body if overtaken. The first lipids/oils removing step is undertaken during the steam/boiling stage, which removes about 15–25% (by weight) of the total lipids/oils contained in the raw materials. The second lipids/oils removing step is conducted by a further steaming/boiling treatment after the comminution of the bones, which removes 25–30% (by weight) of the total lipids/oils. Final lipids/oils removing step is completed by adding lipase to conduct enzymatic decomposition, which removes 25–30% (by weight) of the total lipids/oils. After these three lipids/oils removing steps, the lipids/oils content in the final product is less than 3% of the total weight of the final products.

In order to provide final products in a sterilization manner, the process in accordance with the present invention comprises the following sterilizing steps: 1) steaming/boiling of the whole bones; 2) adding dry ice to decrease the temperature in order to reduce the proliferation of bacteria during the comminution of the raw materials; 3) heating the materials during the deactivation of enzyme; and 4) conducting pasteurization during the homogenization of the product and deodorization.

Another feature of the present invention is to utilize β-cyclodextrin as deodorizing agent. Utilizing the β-cyclodextrin can eliminate the fishy odor of the final product and increases preserving time of the final product is extended.

BEST MODES FOR CARRYING OUT THE INVENTION

The process in accordance with the present invention comprises four basic stages: mechanical comminution and lipids/oil removing by steaming/boiling, bio-chemical extraction and acidic activation, homogenizing and deodorization, and spray drying.

In the mechanical comminution and lipids/oils removing by steaming/boiling stage. appropriate pressure is maintained to remove as much lipids/oils as possible. In one preferred embodiment, the raw material of animal bones is heated to about 120° C. for about 60 minutes with pressure at about 0.12 mPa, and then, the lipids/oils is discharged to obtain processed bones. Thus, obtained bones are mechanically comminuted and heated to a temperature of about 120° C., with pressure at about 0.12 mPa for another 60 minutes in order to further remove lipids/oils. The resulted particles of bones are further milled to fine particles with average particle size within the range of about 0.0074 mm or less to form a bone slurry.

In order to minimize the lipids/oil contents in the final product, the method in accordance with the present invention also adopts an enzymatic decomposition of the lipids/oils by adding lipase to the bone slurry before conducing the bio-chemical extraction and acidic activation. In the bio-chemical extraction and activation stage, the bone slurry is pumped into a bio-chemical reactor and heated to a temperature of about 80° C. for about 10 minutes to sterilize bacteria. Then, 6,000 unit/gram of lipase is added to the slurry with gentle agitation under a temperature of about 40° C., at about pH=7.0. The reaction is maintained for about one hour to decompose the lipids/oils in the bone slurry into glycerin and/or fatty acids. The total amount of the added lipase is in a range of about 0.7–0.9% of the total weight of the bones in the slurry. Then, the supernatant which contains lipids/oils is discharged from the reactor.

The mechanism of lipase reacting with lipid molecular in this lipids/oils removing stage is as follows:

Lipids→Glycerin+Fatty Acid

After the supernatant is discharged, 12,000 unit/gram neutral protease 1.398 is added to the reactor under the condition of 40° C., pH=7.0 with gentle agitation The protease 1.398 quickly reacts with the proteins in the reactor to produce peptides with comparatively large molecular weight. This reaction is maintained for about 1 hour to produce a primary enzymatic decomposed liquid mainly containing peptides. The total amount of the added neutral protease is about 0.07–0.09% by weight of the bones in the reactor.

In order to reduce the peptides in the primary enzymatic decomposed liquid into peptides with small molecular weight and/or amino acids, 1,000,000 unit/gram papain is added to the reactor under the condition of a temperature at about 55° C., pH=6.0 with gentle agitation. This reaction is allowed to proceed for about one hour to obtain a secondary enzymatic decomposed liquid. The total papain added into the reactor is about 0.08–0.10% of the bones in the reactor. Papain is a readily available enzyme which reacts on peptide to produce small peptide and/or amino acids.

In the above discussed two steps of enzymatic reaction, the mechanism of the reaction carried by the protease is as follows:

—CHR'—CO—NH—CHR'—+H$_2$O ... CHR'—COOH+NH$_2$—CHR"

—CHR'—CO—NH—CHR"—+H$_2$O ... CHR'—COOH+$^+$NH$_3$—CHR"

Then, the process in accordance with the present invention is proceeded to an critical step, ie. the acidic activation. Under normal condition, calcium in bones are presented as complex compound between the large organic moleculars in a form of calcium hydrophosphate. When the large organic moleculars are decomposed, the calcium hydrophosphate is released. But, this calcium hydrophosphate has a poor solubility. The calcium contained therein can not be absorbed by human body. The present invention discovered that the calcium contained in the calcium hydrophosphate can be converted into a readily absorbable ions by acidic activation. The mechanism of the acidic activation for releasing Ca$^{2+}$ and other mineral ions is as follows:

Ca(OH)PO$_3$+H$^+$ ... Ca$^{2+}$+PO$_3^-$+H$_2$O

The acids added into the secondary enzymatic decomposed liquid is a mixture of acids, with 31% edible hydrogen chloride: 85% lactic acid: 99% malic acid=1:10:10. The total amount of the acids added in this step is in the range of about 10–12% (by weight) of the bones in the reactor, at a temperature of 70±1° C., pH=2–4, with gentle agitation for about 1.5 hours.

During this acidic activation, calcium released from the calcium hydrophosphate is chelated with the small peptides and/or amino acids produced, whereby to form peptide-calcium chelates and amino acid-calcium chelates, respectively. The mechanism of this reaction is as follows:

+NH3—CHR—COO-+—OOC—CHR'-+NH3 ...

The added edible hydrogen chloride is in a low concentration, while the organic acid added is in a high concentration. This combination not only reduces the Cl$^-$ ions presented in the final products, but also produces supplemental organic calcium, such as lactic calcium and malic calcium.

The resulted acidic liquid is neutralized by the addition of edible calcium hydroxide to a pH in a range of about 6.5–7.0. This neutralization is necessary because it makes the secondary enzymatic decomposed liquid to be neutral to meet the standard of edible products.

In addition, calcium hydroxide is used to replace the conventional sodium hydroxide for neutralization in the present invention. This replacement brings the benefit of reducing the sodium content, as well as increasing the calcium content in the final product. It has been a standard that the sodium content should be as less as possible in health supplement products.

In the homogenization and deodorization stage, the neutralized secondary enzymatic decomposed liquid is centrifuged at a speed of 2,000–2,500 rpm to separate large bone pieces/particles. Resulted bone slurry is transported into thermal container. About 2.05–5.0%, preferably 3.0% of β-cyclodextrin by weight of total bones in the thermal reactor is added. Under the condition of a temperature of 65–70° C. and pressure of 12–23 mPa, the bone slurry is fully agitated and homogenized in a homogenizer. The resulted slurry is an enzymatic decomposed product of bone having particles size of 0.038 nmm or less.

The resulted homogenized secondary enzymatic decomposed slurry is pumped into a thermal container and heated to a temperature of about 80° C. for about 10 minutes for pasteurization.

Finally, the pasteurized product is spray dried in a spray tower to obtain a powder product readily for absorption by human body. This final product is rich in bio-organic calcium without unpleasant odor.

BEST MODE

One of the preferred embodiment of the process in accordance with the present invention for producing bio-organic calcium composition from animal bones is illustrated by the flow chart as below:

Fresh Animal Bones→Washing→Frozen→First Steaming/Boiling→Meat Removing→Rinse and Cooling→Milling→Second Steaming/Boiling→Fine Milling →Super Fine Milling→Screening→Bio-Chemical Removing of Lipids→Primary Protease Decomposition→Secondary Protease Decomposition→Acidic Activation→Centrifuge→Deodorizing→Homogenizing→Pasteurization→Spray Drying.

In one preferred embodiment, fresh beef vertebrate bones and ribs are used as raw material. The fresh beef vertebrate bones and ribs are stored at −18° C. When used, the fresh beef vertebrate and ribs are taken out from the freezer and stayed at room temperature for about 10–20 minutes. These raw materials are put into a cooking container and heated to a temperature of 120° C. Maintaining this temperature for about 60 minutes at a pressure of 0.12 mPa. Then, the valve for providing steam is shut off. The vent valve is opened until the pressure gauge back to zero. About 10 minutes later. lipids and water are discharge form the cooking container. This treatment also makes the bones easier to be comminuted later.

After the first steaming/boiling treatment, bones are taken out from the cooking container. Meats are taken off from the bones. Cold water is used to rinse the bones and make the temperature of the bones to ambient temperature. Then, the bones are milled. After this milling, the bones are returned to the cooking container and heated to a temperature of 120° C. at a pressure of about 0.12 mPa for 60 minutes in order to further remove lipids.

Then, the bones are further milled to form a bone slurry of which the fine particulate of bones are in size less than 0.074 mm. In this milling step, the water and bones are in the rate of about 1:1.7. In order to minimize the proliferation of bacteria during this milling step, dry ice is added to the mill in an amount of about 6–10 Kg dry ice/100 Kg bones.

The resulted bone slurry passes the shaking screen with 0.074 mm diameter and pumped into a bio-chemical reactor. Adjusting the pH of the bones slurry to 6.5–7.5, preferable 7.0. Then, the bone slurry is heated to about 80° C. and maintained at this temperature for about 10 minutes. 6,000 unit/gram neutral lipase is added to the bones slurry at the condition of 40° C., pH=7.0, with gentle agitation. This enzymatic decomposition is allowed to carry on for about one hour. The lipase added is in an amount of 0.7–0.9% of the weight of the net bones. After this enzymatic decomposition, supernatant is discharged from the reactor.

Water is re-filled into the reactor in an amount of water:bones=1:1.7. Then, under the condition of gentle agitation, 40° C. temperature and pH=7.0, 12,000 unit/gram 1.398 neutral protease is added into the bone slurry in an amount of 0.07–0.09% of the total weight of the bones. This reaction is carried for about 1 hour.

Under the condition of gentle agitation, 55° C. temperature and pH=6.0, 1.000,000 unit/gram papain is added into the bone slurry in an amount of 0.08–0.10% of the total weight of the bones. This reaction is proceeded for about one hour to make the primary enzymatic decomposed liquid becoming secondary enzymatic decomposed liquid.

Acidic activation is carried out by adding a acids mixture of 20% edible hydrogen chloride: 85% lactic acid: 85% malic acid=1:10:10 under gentle agitation and 70° C. (±1° C.) temperature into the secondary enzymatic decomposed liquid. This reaction is proceeded under the condition of 70° C. (±1° C.) temperature. pH=2.0–4.0, preferable pH=2.0 for about 1.5 hours.

Calcium hydroxide is utilized to neutralize the secondary enzymatic decomposed liquid and make the pH of the secondary enzymatic decomposed liquid maintained in a range of about 6.5–7.0.

The resulted secondary enzymatic decomposed liquid is centrifuged to obtain a bone slurry containing bone particles of size less than 0.038 mm. After the centrifugation, the secondary enzymatic decomposed liquid is homogenized by a homogenizer. Then, the homogenized secondary enzymatic decomposed liquid is pumped into a thermal container and heated to a temperature of 80° C. (±1° C.) for pasteurization. β-cyclodextrin is added therein in an amount of 2.0–5.0%, preferable 3.0% of the total weight of bones with gentle agitation for about 10 minutes.

After the pasteurization, the bone slurry is spray dried in a spray drying tower to result in a final product in powder form. This final product is rich in proteins, bio-organic calcium, such as peptide-calcium chelates and amino acid-calcium chelates, as well as other organic calcium and inorganic calcium.

The final products contains bio-organic calcium in a range of at least 150 mg/kg, preferably in a range of at least 165 mg/kg, most preferably in a range of at least 175 mg/kg by weight of the total composition. Lipids content in the final products is in a amount of less than 10%, preferably less than 7%, and most preferably less than 4% by weight of the total composition.

EQUIVALENT

It is understood that the previous descriptions and explanations are given by way of example, and that numerous changes in the combinations of elements and functions as well as changes in design may be made without departing from the spirit and scope of the present invention as hereinafter claimed. These and other modifications to and variations upon the embodiments described above are provided for by the present invention, the scope of which is limited only by the following claims.

What is claimed is:

1. A process of producing a bioorganic calcium composition from animal bones comprises the steps of:
   a) removing lipids from the animal bones by steaming/boiling treatment;
   b) comminuting the bones resulted from the step a) to form a bone slurry;
   c) adding neutral lipase into the slurry for further removing lipids;
   d) adding neutral protease into the slurry obtained from the step c) to form a primary enzymatic decomposed liquid;
   e) adding papain into the primary enzymatic decomposed liquid to form a secondary enzymatic decomposed liquid;
   f) acidifying said secondary enzymatic decomposed liquid to produce a bioorganic calcium composition.

2. The process as recited in claim 1, wherein said step f) further includes a step of adding acid mixture into said secondary enzymatic decomposed liquid in an amount of 10–12% of the total bones by weight and maintaining the temperature at 70° C. (±1° C.), pH=2–4 with gentle agitation for about 1.5 hours.

3. The process as recited in claim 2, wherein said acid mixture has a weight ratio of 20% edible hydrogen chloride: 85% lactic acid: 85% malic acid=1:10:10.

4. The process as recited in claim 1 further comprises step g): neutralizing the pH of the product resulted in step f) to produce a neutral product.

5. The process as recited in claim 4, wherein said step g) further comprises adding calcium hydroxide to said product to adjust the pH of said product to a range of 6.5–7.0.

6. The process as recited in claim 5 further comprises centrifugation and homogenization of said neutral product.

7. The process as recited in anyone of the claims 4 or 6, wherein said process further comprises step h): deodorizing said neutral product by addition of deodorizing agent.

8. The process as recited in claim 7, wherein said deodorizing agent comprises β-cyclodextrin in an amount of 2–5% by weight of the total liquid.

9. The process as recited in claim 8, wherein said step of addition of β-cyclodextrin further comprises maintaining said neutral product at a temperature of 80° C. for about 10 minute with gentle agitation.

10. The process as recited in claim 9 further comprises a step of spray drying of said neutral product.

11. The process as recited in claim 1, wherein said animal bones are fresh beef vertebrate and/or ribs.

12. The process as recited in claim 11, wherein said step a) further comprises a treatment of said fresh beef vertebrate and/or ribs by steaming/boiling at a temperature of about 120° C., pressure of 0.12 mPa for about 60 minutes.

13. The process as recited in claim 1 further comprises a step of taking off meat from said animal bones after said step a) but prior to said step b).

14. The process as recited in claim 13 further comprises storing said animal bones at a temperature of −12° C. for frozen after said animal bones being processed by said steaming/boiling.

15. The process as recited in claim 14, wherein said step b) further comprises a step of treating of said animal bones with steam/boiling water at a temperature of 120° C., pressure of 0.12 mPa for about 60 minutes.

16. The process as recited in claim 15, wherein said comminuting of said animal bones further comprises addition of dry ice in an amount of 6–10 kg dry ice/100 Kg animal bones.

17. The process as recited in claim 16 further comprises passing said bone slurry to a screen with 0.074 mm diameter.

18. The process as recited in claim 1, wherein said step c) further comprises following steps:

heating said bone slurry to a temperature of 80° C. for about 10 minutes;

adjusting the pH of the bone slurry to 6.5–7.0; and further removing lipid from said bone slurry by addition of 6,000 unit/gram neutral lipase in an amount of 0.7–0.9%(weight) of the total bones while gently agitating the slurry and maintaining temperature at about 40° C. for about one hour.

19. The process as recited in claim 1, wherein said step d) further comprises steps of:

adjusting pH of said bone slurry to 6.5–7.0; and conducting enzymatic decomposition of said bone slurry by addition of 12.000 unit/gram neutral protease in an amount of 0.07–0.09%(weight) of the total bones while gently agitating the slurry and maintaining temperature at about 40° C. for about one hour to carry out said enzymatic decomposition of protein and produce a primary enzymatic decomposed liquid.

20. The process as recited in claim 1, wherein said step e) further comprises the steps of:

adjusting pH of said primary enzymatic decomposed liquid to 5.5–6.5; and conducting an enzymatic decomposition of said primary enzymatic decomposed liquid by addition of 1,000,000 unit/gram papain in an amount of 0.08–0.1 0%(weight) of the total bones while gently agitating the slurry and maintaining temperature at about 55° C. for about one hour to carry out said second enzymatic decomposition and produce a secondary enzymatic decomposed liquid.

* * * * *